US012612594B2

(12) United States Patent
Qiang et al.

(10) Patent No.: US 12,612,594 B2
(45) Date of Patent: Apr. 28, 2026

(54) *BIPOLARIS YAMADAE* (Y. NISIK.) SHOEMAKER, AND SCREENING AND IDENTIFICATION METHOD THEREFOR AND USE THEREOF

(71) Applicant: NANJING AGRICULTURAL UNIVERSITY, Jiangsu (CN)

(72) Inventors: Sheng Qiang, Jiangsu (CN); Min Tan, Jiangsu (CN)

(73) Assignee: NANJING AGRICULTURAL UNIVERSITY, Jiangsu (CN)

( * ) Notice: Subject to any disclaimer, the term of this patent is extended or adjusted under 35 U.S.C. 154(b) by 634 days.

(21) Appl. No.: 17/967,840

(22) Filed: Oct. 17, 2022

(65) Prior Publication Data

US 2023/0203429 A1　Jun. 29, 2023

Related U.S. Application Data

(63) Continuation of application No. PCT/CN2021/087342, filed on Apr. 15, 2021.

(30) Foreign Application Priority Data

Apr. 17, 2020　(CN) ......................... 202010303803.X

(51) Int. Cl.
| | |
|---|---|
| *C12N 1/14* | (2006.01) |
| *A01N 63/30* | (2020.01) |
| *C12N 1/145* | (2026.01) |
| *C12Q 1/6895* | (2018.01) |
| *C12R 1/645* | (2006.01) |

(52) U.S. Cl.
CPC ........... *C12N 1/145* (2021.05); *C12Q 1/6895* (2013.01); *A01N 63/30* (2020.01); *C12R 2001/645* (2021.05)

(58) Field of Classification Search
CPC ...... C12N 1/145; C12Q 1/6895; A01N 63/30; C12R 2001/645; A01P 13/02
See application file for complete search history.

(56) References Cited

FOREIGN PATENT DOCUMENTS

| | | |
|---|---|---|
| CN | 107418900 | 12/2017 |
| CN | 108624514 | 10/2018 |
| CN | 110055303 | 7/2019 |
| CN | 111518702 | 8/2020 |
| KZ | 20997 | 3/2009 |

OTHER PUBLICATIONS

Machado, Ana Carolina Ribeiro, et al. "Formulation and pathogenicity of a bioherbicide for wild poinsettia control." African Journal of Microbiology Research 14.4 (2020): 129-135. Published: Apr. 30, 2020. DOI: 10.5897/AJMR2020.9321 Article No. 5379E4863532 ISSN: 1996-0808 (Year: 2020).*
Mubashar Raza et al., "Culturable plant pathogenic fungi associated with sugarcane in southern China", Fungal Diversity, Oct. 16, 2019, pp. 1-14, vol. 99.
Marin-Felix Y et al., "New species and records of Bipolaris and Curvularia from Thailand", Mycosphere, Oct. 18, 2017, pp. 1555-1573, vol. 8.
Qin, Jian et al., "Pathogen identification of a Bipolaris leaf spot in Momordica charantia", Acta Phytopathologica Sinica, Mar. 27, 2019, with English abstract thereof, pp. 711-714, vol. 49, No. 5.
Toyozo Sato, "Studies on taxonomy and identification of plant pathogenic fungi based on morphology and phylogenetic analyses, and fungal pathogenicity focused on the host specificity", Journal of Japanese Society of Plant Pathology, Aug. 2016, with English abstract thereof, pp. 160-165, vol. 82, No. 3.
Katia De Lima Nechet et al., "Bipolaris euphorbiae as a biological control agent for wild poinsettia (*Euphorbia heterophylla*): host-specificity and variability in pathogen and host populations", Biocontrol, Apr. 2006, pp. 259-275, vol. 51.
Xiaofang Sun; et al., "Etiology and Symptoms of Maize Leaf Spot Caused by *Bipolaris* spp. in Sichuan, China," Pathogens., vol. 9, No. 3:229, Mar. 20, 2020, pp. 1-18.
"International Search Report (Form PCT/ISA/210) of PCT/CN2021/087342," mailed on Jul. 19, 2021, with English translation thereof, pp. 1-7.
"Written Opinion of the International Searching Authority (Form PCT/ISA/237) of PCT/CN2021/087342," mailed on Jul. 19, 2021, pp. 1-3.

* cited by examiner

*Primary Examiner* — Kade Ariani
(74) *Attorney, Agent, or Firm* — JCIPRNET

(57) ABSTRACT

A *Bipolaris yamadae* (Y. Nisik.) shoemaker (HXDC-1-2), and a screening and identification method therefor and use thereof. The *Bipolaris yamadae* (Y Nisik.) strain (HXDC-1-2) is deposited in the China General Microbiological Culture Collection Center with the accession number CGMCC No. 17778. The *Bipolaris yamadae* (Y. Nisik.) strain (HXDC-1-2) is applied to biological weed control when the conidial concentration is $10^2$ conidia/ml or more.

5 Claims, 3 Drawing Sheets

Specification includes a Sequence Listing.

SEQUENCE LISTING

Sequence total quantity: 11
SEQ ID NO: 1            moltype = DNA   length = 572
FEATURE                 Location/Qualifiers
source                  1..572
                        mol_type = genomic DNA
                        organism = Bipolaris yamadae
SEQUENCE: 1
ttaagttcag cgggtatccc tacctgatcc gaggtcaaaa gttaaaattt gtagagtctt   60
gatggattac cgtccttttc tcctgacaca gagtgcaaaa tatgtgctgc gctccgaaac  120
cagtaggccg gctgccaatc gttttaaggc gagtctccca gcaagaggga gacaaaaaac  180
gcccaacacc aagcaaagct tgaaggtaca aatgacgctc gaacaggcat gccctttgga  240
ataccaaagg gcgcaatgtg cgttcaaaga ttcgatgatt cactgaattc tgcaattcac  300
actacgtatc gcatttcgct gcgttcttca tcgatgccag aaccaagaga tccgttgttg  360
aaagttgtaa taattacatt gttttttact gacgctgatt gcaactgcat tagaaaaagg  420
tttatggttt ggtcctggtg gcgggcgaac ccgcccagga aacaacaagt ggcgaaaaga  480
catgggtgaa aaaaatattt cagccggccg cgaagccaaa gccttcatat tttcgttgtg  540
taatgatccc tccgcaggtt cacctacgga ga                                 572

SEQ ID NO: 2            moltype = DNA   length = 577
FEATURE                 Location/Qualifiers
source                  1..577
                        mol_type = genomic DNA
                        organism = Bipolaris yamadae
SEQUENCE: 2
aagaggcgtt ggagagtacc tcgatgtcgg gcttgtaggt ctcgtggttg acacccatga   60
cgaacatggg ggcgtcagcg gagggagcag agatgacaac cttcttggct ccgcccttca  120
agtgggcctt ggccttctcg gtggtggtga agacaccggt agactcgacg acgtagtagg  180
cgccagtctc gctccatgga atgttggcgg ggtccttctc catgtggaaa cggatagtct  240
tgccgttgac ggtcaggttg ttgccgtcaa ccttgatgtc acccttgaac tggccgtgtg  300
tgctgtcata cttgagcatg tatgcctgtg tatacgtcag tctgcatggt tccatcaaag  360
aaatgacacc agtgcgtcag gccgaagcag acgcttgctg tgatgaaagg ttctgggttg  420
agggagtgct tacagcgtag tggggctcga tgaaaggtgt gtttacggcg acaatgtcga  480
cgtcgttgtg ctcgatgctg agatatgggg tcagctttgg tgtgcgtaaa atggacaaac  540
cccaaggata cttacgcatt gcggaagacg atgcggc                            577

SEQ ID NO: 3            moltype = DNA   length = 770
FEATURE                 Location/Qualifiers
source                  1..770
                        mol_type = genomic DNA
                        organism = Bipolaris yamadae
SEQUENCE: 3
caagaacatg atcactggta cctcccaggc tgactgcgct atcctcatta tcgctgccgg   60
tactggtgag ttcgaggctg gtatctccaa ggatggccag actcgtgagc acgcccttct  120
cgcctacacc cttggtgtca agcagctcat cgttgccatc aacaagatgg acaccaccaa  180
gtggtctgag gaccgttacc aggagatcat caaggagacc tccaacttca tcaagaaggt  240
cggctacaac cccaagcacg ttcccttcgt gcccatctcc ggtttcaacg gtgacaacat  300
gattgaggcc tccaccaact gccccctggta caagggttgg gagaaggaga ccaagtccaa  360
ggccaccggt aagaccctcc tcgaggccat cgatgccatc gaccctccca gccgtcctac  420
cgacaagccc ctccgtcttc ccctccagga tgtgtacaag atcggtggta ttggcacggt  480
tcccgtcggt cgtgtcgaga ccggtatcat caaggccggt atggtcgtca ccttcgcccc  540
cgctggtgtc accactgaag tcaagtccgt cgagatgcac cacgagcagc tgaccgaggg  600
tgtccccggt gacaacgtcg gcttcaacgt caagaacgtc tccgtcaagg agatccgtcg  660
tggtaacgtt gctggtgact ccaagaacga cccccccaag gcttccgagt ccttcaacgc  720
ccaggtcatc gtcctcaacc accccggtca ggtcggtgcc ggttacgcac              770

SEQ ID NO: 4            moltype = DNA   length = 20
FEATURE                 Location/Qualifiers
source                  1..20
                        mol_type = other DNA
                        organism = synthetic construct
SEQUENCE: 4
tcctccgctt attgatatgc                                               20

SEQ ID NO: 5            moltype = DNA   length = 22
FEATURE                 Location/Qualifiers
source                  1..22
                        mol_type = other DNA
                        organism = synthetic construct
SEQUENCE: 5
ggaagtaaaa gtcgtaacaa gg                                            22

SEQ ID NO: 6            moltype = DNA   length = 20
FEATURE                 Location/Qualifiers
source                  1..20
                        mol_type = other DNA
                        organism = synthetic construct
SEQUENCE: 6
caacggcttc ggtcgcattg                                               20

-continued

```
SEQ ID NO: 7          moltype = DNA  length = 19
FEATURE               Location/Qualifiers
source                1..19
                      mol_type = other DNA
                      organism = synthetic construct
SEQUENCE: 7
gccaagcagt tggttgtgc                                      19

SEQ ID NO: 8          moltype = DNA  length = 23
FEATURE               Location/Qualifiers
source                1..23
                      mol_type = other DNA
                      organism = synthetic construct
SEQUENCE: 8
gcyccygghc aycgtgaytt yat                                 23

SEQ ID NO: 9          moltype = DNA  length = 23
FEATURE               Location/Qualifiers
source                1..23
                      mol_type = other DNA
                      organism = synthetic construct
SEQUENCE: 9
atgacaccra crgcracrgt ytg                                 23

SEQ ID NO: 10         moltype = DNA  length = 24
FEATURE               Location/Qualifiers
source                1..24
                      mol_type = other DNA
                      organism = synthetic construct
SEQUENCE: 10
cgccagggtt ttcccagtca cgac                                24

SEQ ID NO: 11         moltype = DNA  length = 24
FEATURE               Location/Qualifiers
source                1..24
                      mol_type = other DNA
                      organism = synthetic construct
SEQUENCE: 11
agcggataac aatttcacac agga                                24
```

BIPOLARIS YAMADAE (Y. NISIK.) SHOEMAKER, AND SCREENING AND IDENTIFICATION METHOD THEREFOR AND USE THEREOF

CROSS REFERENCE OF RELATED APPLICATION

The present application is a continuation application of international PCT application serial no. PCT/CN2021/ 087342, filed on Apr. 15, 2021, which claims priority to Chinese patent application No. 202010303803.X filed on Apr. 17, 2020 and entitled "*Bipolaris yamadae* (Y. NISIK.) SHOEMAKER, AND SCREENING AND IDENTIFICATION METHOD THEREFOR AND USE THEREOF", the disclosure of which is hereby incorporated by reference in the present application.

REFERENCE TO A SEQUENCE LISTING

The instant application contains a Sequencing Listing which has been submitted electronically in XML file and is hereby incorporated by reference in its entirety. Said XML copy, created on Jul. 22, 2025, is named 127937_ SEQUENCELISTING and is 12,865 bytes in size.

TECHNICAL FIELD

The present disclosure relates to the field of microbiological techniques for agricultural plant protection and crop weed control, in particular to a *Bipolaris yamadae* (Y. Nisik.) Shoemaker strain (HXDC-1-2), and a screening and identification method therefor and a use thereof.

BACKGROUND

Damage caused by weeds is one of the most important factors leading to crop yield cuts, resulting in $95 billion in global agricultural losses each year. The area of weed damage in China's farmland is about 78.8 million hectares, which still causes losses of 14.6 million tons of grain, cotton and oil, and direct economic losses of nearly 100 billion yuan under the annual investment of 23.5 billion yuan in weed control costs. *Echinochloa crusgalli* (L.) Beauv, *Avena fatua* L., *Alopecurus aequalis* Sobol., *Digitaria sanguinalis* (L.) Scop., *Leptochloa chinensis* (L.) Nees, *Eleusine indica* (L.) Gaertn., *Setaria viridis* (L.) Beauv., *Chenopodium album* L., *Monochoria vaginalis* (Burm.f.) Presl. are the worst ten weeds in the farmland, of which the *gramineae* accounts for 80%. Efforts to control weeds have never ceased since humans began to engage in agricultural production. In the early 1950s, chemical herbicides developed rapidly due to their convenient use and quick effect. With the widespread use of chemical herbicides, the negative effects are becoming increasingly apparent. The heavy application of chemical herbicides has brought about an environmental pollution crisis. The application of long residual effect herbicides has caused residual toxicity, which leads to reduced yields of the next crop and even land degradation. More than 100 chemical herbicides have been banned or deregistered in more than 30 countries worldwide. In addition, herbicide-resistant weed populations evolve.

Biological herbicide refers to the application of large doses of biological pesticides artificially mass-produced under artificial control to control weeds. There are two significant characteristics: First, a large number of biological inoculums are obtained through large-scale technical pro duction; Second, a rapid infection is achieved and the weeds are killed in a short period time by a submerged application. In 1981, DeVine was registered as the first biological herbicide in United States. DeVine is a chlamydospore suspension liquid of the disease-causing strain of *Phytophthora palmivora* native of Florida, USA, which is used to control the weeds *Morrenia odorata*, with a 90% efficacy and a validity period up to 2 years, and is widely used in Florida's orangeries. Subsequently, Collego was registered and put into practice. The intervention of genetic engineering and cell fusion technology can recombine the excellent herbicidal genes that exist in nature (such as strong disease and toxin production), providing the possibility of improving biological herbicide varieties, improving control efficacy and improving host specificity. In addition to the current commercial biological herbicides developed in the 1980s, Camperico and Biochon were launched in the late 1990s, these current commercial biological herbicides have played an important role in controlling the corresponding target weeds, or even the only option. Among the candidate biocontrol fungi that have been studied are relatively concentrated in the following genera: there are 18 species of *Colletotrichum* sp., 13 species of *Fusarium* sp., 12 species of *Alternaria* sp., 8 species of *Cercospora* sp., *Puccinia* sp., *Sclerotinia* sp., *Entyloma* sp., *Ascochyta* sp. The main successful and patented species used in crop production at present are *Colletotrichum* species (U.S. Pat. Nos. 3,849,104 and 3,999,973); *Fusarium* species (U.S. Pat. No. 4,419,120); *Alternaria* species (U.S. Pat. No. 4,390,360); *Ascochyta* species (U.S. Pat. No. 4,915,724) and *Selerotinia* species (CAOZ, 292,233); *Sclerotium rolfsii* (SC64), and the like. At present, there are patents in China and abroad for the use of *Bipolaris* sp. in biological herbicides, such as *Bipolaris setariae, Bipolaris maydis*, and *Bipolaris panici-miliace*. And there are no reports on the application of *Bipolaris yamadae*, nor on the biological control of gramineous weeds and lawn weeds in crop fields, as well as the biological control of *Microstegium vimineum* and its relatives.

SUMMARY

The objectives of the exemplary embodiments disclosed in the present disclosure is to provide a *Bipolaris yamadae* (Y. Nisik) Shoemaker strain and a screening and identification method therefor and a use thereof, with respect to the weeds in the crop fields such as *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials, fruit trees (including the gramineous weeds such as *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, and *Microstegium vimineum*; the annual *cyperaceae* weeds such as *Cyperus iria* L., *Cyperus michelianus* (L.) Link, and *Cyperus compressus* L; the broad-leaved weeds such as *Humulus scandens* (Lour.) Merr., *Aeschynomene indica* L., *Chenopodium album* L. and *Chenopodium serotinum* L. The strain is used for biological weed control, which has the advantages of high efficiency of weeding, environmental protection without residue, low cost, no pollution, high safety of crops and obvious control effects.

The present disclosure discloses a *Bipolaris yamadae* (Y. Nisik.) Shoemaker strain, a screening and identification method therefor and a use thereof. The adopted technical solutions are as follows.

Provided is a *Bipolaris yamadae* (Y. Nisik.) Shoemaker strain, the strain is *Bipolaris yamadae* (Y. Nisik.) Shoemaker HXDC-1-2 and is preserved in the China General Microbiological Culture Collection Center with a preservation number CGMCC No. 17778.

In one embodiment, the diameter of the colony formed by the strain ranges from 50 to 60 mm; the upper surface of the colony is gray-black, the rear surface of the colony is black-brown, and the colony does not contain any water-soluble pigment; the strain includes conidiophores, wherein the conidiophores are solitary or clustered, olive green or yellow-brown, the apex of the conidiophores is light-colored, the conidiophores are in a curved shape, and the width of the conidiophores ranges from 4.5 to 9.5 μm; the strain further includes conidia, the conidia are colored from yellow-brown to dark-brown, are spindle-shaped or club-shaped, and are straight or slightly curved, the middle portions of the conidia are slightly wider, and two apices of the conidia are slightly narrower, the basal cells of the conidia are blunt round, the outer surfaces of the basal cells are smooth, the basal cells have 6 to 9 pseudoseptum, and the outer surfaces have an area of 54.5 to 92.5 μm×12.5 to 17.5 μm.

The exemplary embodiments disclosed in the present disclosure provide a method of screening and identifying the *Bipolaris yamadae* (Y. Nisik.) Shoemaker strain. The method includes the following steps.

In Step 1), the strain is placed and cultivated in a dark incubator at 28° C. for four days, fresh mycelia were scraped from the surface of a colonized plate and genomic DNA was extracted using the Fungal gDNA Isolation Kit. The molecular identification of strain HXDC-1-2 was carried out using an internal transcribed spacer (ITS), glyceraldehyde-3-phosphate dehydrogenase (GPDH) and elongation factor 1-alpha (EF1α) gene. General primers ITS4 and ITS5, GPDI and GPD2, EF1-983F and EF1-2218R were used to amplify the rDNA genes of strain, wherein,

```
                                       (SEQ ID NO: 4)
ITS4:  5'-TCCTCCGCTTATTGATATGC-3';

(SEQ ID NO: 5)
ITS5:  5'-GGAAGTAAAAGTCGTAACAAGG-3;

(SEQ ID NO: 6)
GPD1:  5'-CAACGGCTTCGGTCGCATTG-3';

(SEQ ID NO: 7)
GPD2:  5'-GCCAAGCAGTTGGTTGTGC-3';

(SEQ ID NO: 8)
EF1-983F:  5'-GCYCCYGGHCAYCGTGAYTTYAT-3';
and (SEQ ID NO: 9)
EF1-2218R:  5 '-ATGACACCRACRGCRACRGTYTG-3'.
```

In Step 2), PCR products obtained in Step 1) were extracted and purified with the DNA Gel/PCR Purification Miniprep Kit. The purified products were ligated to the pMD19 T-vector and transformed into *Escherichia coli* DH5a competent cells, white colonies are selected after blue and white spot screening and then are shaked. PCR amplification is carried out and is detected by the electrophoresis and gel analyzer. A single bright band is displayed on 2% agarose gel. The positive clones were picked by the blue-white screening technique and sequenced using the M13 primers, wherein,

```
                                      (SEQ ID NO: 10)
M13-F:  5'-CGCCAGGGTTTTCCCAGTCACGAC-3'

(SEQ ID NO: 11)
M13-R:  5'-AGCGGATAACAATTTCACACAGGA-3'
```

In Step 3), the sequences of the DNA fragments obtained in Step 2) were assembled using DNAMAN software. ITS, GPDH and EF1α sequences of the fungal HXDC-1-2 strain were compared with the sequences available in the NCBI nucleotide database using BLAST search program to obtain its taxonomy.

In Step 4), after the PCR amplification, the sequencing and the comparison, the fungal strain HXDC-1-2 was therefore classified to *Bipolaris yamadae* (Y. Nisik.) Shoemaker, when the homology of the EF1α amplified sequence with respect to *Bipolaris-yamadae*-model strain ACCC36334 is equal to or greater than 99%, respectively; the homology of the ITS amplified sequence with respect to *Bipolaris-yamadae*-model strain CPC28807 is equal to or greater than 99%; or when the homology of the GPDH amplified sequence with respect to the *Bipolaris-yamadae*-model strain CPC28807 is equal to or greater than 99%.

The above molecular markers can also be used as primers for detection. This strain can be determined when the homology of the above molecular marker sequence and the *Bipolaris-yamadae*-model strain CPC28807 is 99%.

In one embodiment, the ITS amplified sequence is as shown in SEQ ID NO: 1, the GPDH amplified sequence is as shown in SEQ ID NO: 2, and the EF1α amplified sequence is as shown in SEQ ID NO: 3. However, the molecular markers of the present disclosure are not limited to this.

Use of the *Bipolaris yamadae* (Y. Nisik.) Shoemaker strain as a biological herbicide is provided in the present disclosure.

In the use of the *Bipolaris yamadae* (Y. Nisik.) Shoemaker strain as a biological herbicide, the conidial suspension of the *Bipolaris yamadae* (Y. Nisik.) Shoemaker strain (HXDC-1-2) with the conidial concentration of equal to or greater than $10^2$ conidia/ml are inoculated on the target weeds in crop field.

In one embodiment, the target weeds include at least one of *gramineae* weeds, *Sedge* weeds and broad-leaved weeds, wherein the *gramineae* weeds include at least one of *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, *Microstegium vimineum* and relatives of the *Microstegium vimineum*; The *Sedge* weeds include at least one of *Cyperus iria* L., *Cyperus michelianus* (L.) Link, *Cyperus compressus* L. The broadleaf weeds include at least one of *Humulus scandens* (Lour.) Merr., *Aeschynomene indica* L., *Chenopodium album* L. and *Chenopodium serotinum* L. However, the species of weeds in the present application are not limited to this.

In one embodiment, the relatives of the *Microstegium vimineum* include at least one of the *Microstegium nodosum* (Kom.) Tzvel., *Microstegium ciliatum* (Trin.) A. Camus, *Microstegium japonicum*, and *Arthraxon hispidus* (Thunb.) Makino.

In one embodiment, the crops in the crop field include at least one of *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials and fruit trees. However, the species of crops in the present disclosure are not limited to this.

In one embodiment, the vegetables include at least one of *Brassica* chinese L., *Brassica pekinensis* (Lour.) Rupr., *Raphanus sativus* L., Luffa *cylindrica* (L.) Roem., *Solanum melongena* L., *Capsicum annuum* L. The traditional Chinese medicinal material includes at least one of *Perilla frutescens* (L.) Britt., *Nepeta cataria* L. and *Glechoma longituba* (Nakai) Kupr. The fruit trees include *Myrica rubra* (Lour.) S. et Zucc. However, the species of vegetables, traditional Chinese medicinal materials and fruit tree crops in the present application are not limited to this.

The exemplary embodiments of the present disclosure have the following advantages and positive effects.

1. The specialized fungal agent of *Bipolaris yamadae* (Y. Nisik.) Shoemaker strain for biological weeding can be safely selected between crops and gramineous weeds. The herbicides of the present disclosure are environmentally friendly, can inhibit the development of herbicide-resistance in weeds, are conducive to the promotion of green food and organic agriculture, and are low cost, pollution-free, and safe to crops. Among the 30 families 103 species crops or economic plants for the test, there are 33 species that are sensitive to the *Bipolaris yamadae* (Y. Nisik.) shoemaker, 15 species that are slightly sensitive to the *Bipolaris yamadae* (Y. Nisik.) Shoemaker, and 5 species that are insensitive to the *Bipolaris yamadae* (Y. Nisik.) Shoemaker, of which most of the sensitive plants are concentrated in the *gramineae*, and other families of plants such as *legumino-sae, cruciferae, pedaliaceae,* and some *gramineae* are weaker in the sensitivity to the *Bipolaris yamadae* (Y. Nisik.) Shoemaker. Therefore, this strain can be used in *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials, fruit trees and other crop fields to control farmland weeds, including the gramineous weeds such as *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, and *Microstegium vimineum*; the annual *Sedge* such as *Cyperus iria* L., *Cyperus michelianus* (L.) Link, and *Cyperus compressus* L; the broad-leaved weeds such as *Humulus scandens* (Lour.) Merr., *Aeschynomene indica* L., *Chenopodium album* L. and *Chenopodium serotinum* L.

2. The use of the *Bipolaris yamadae* (Y. Nisik.) Shoemaker strain in biological weed control is to use the living creature themselves for screening and identification, which are directly collected from the natural environment and is a natural pathogenic fungus of the target weeds occurring in the target crop field and the environment thereof. Since the living organism already exists in the environment, there is no ecological risk in the process of use. In addition, this strain is highly specialized, safe for crops and other non-target plants, and will not cause residual harm to the environment. The mycelial and conidial cells of the strains are rapidly degraded after death, and the degradation products are recyclable organic compounds and will not lead to contamination. Thus, the strain is environmentally safe and can be used to produce green or organic agricultural products.

3. The control effect of the strain on the target weeds can reach 70% or greater than 70%, and further can reach 80% or greater than 80%, especially the plants at the seedling stage.

4. According to the test, the *Bipolaris yamadae* (Y. Nisik.) Shoemaker strain HXDC-1-2 is safe for most crops, has a weak sensitivity to *Gossypium* spp L., *Triticum aestivum* L. and *Hordeum vulgare* L., and can be safely used in *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials, fruit tree crop fields, and can be used to control the weeds in the above fields (including the grass such as *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, and *Microstegium vimineum*; the annual *Sedge* such as *Cyperus iria* L., *Cyperus michelianus* (L.) Link, and *Cyperus compressus* L.; the broad-leaved weeds such as *Humulus scandens* (Lour.) Merr., *Aeschynomene indica* L., *Chenopodium album* L. and *Chenopodium serotinum* L. This again indicates that *Bipolaris yamadae* (Y. Nisik.) Shoemaker strain HXDC-1-2 can be used as a biological herbicide for the control of *Microstegium vimineum* and gramineous weeds.

DETAILED DESCRIPTION OF THE EMBODIMENTS

As mentioned above, 324 biotypes of 188 weeds have been found to be resistant to 19 types of chemical herbicides in the world, which reduces the efficacy, increases the dosage, increases the cost, and also increases the pollution. The consequence is the simplification of herbicide varieties, thereby increasing the risk of resistance evolution.

The inventors have found that the above deficiencies also enhance the technical demands in the market for the development of broad-spectrum, efficient and low-toxicity new herbicides and the development of biological weeding. Therefore, the development of green herbicides, especially biological herbicides instead of chemical herbicides, is an important way to solve this contradiction. In addition, in comparison with the $100 million development cost of the new chemical herbicides, the cost of developing biological herbicides is dozens or even hundreds of times lower. The agricultural sustainable development strategies implemented in many countries around the world have promoted the development of this technology, and therefore, the development of biological herbicides has become a new way to against these *gramineae* weeds. However, there are currently few effective bioherbicides to target these *gramineae* weeds.

The present disclosure is described in further detail below in combination with the accompanying drawings and embodiments.

Figure 1:
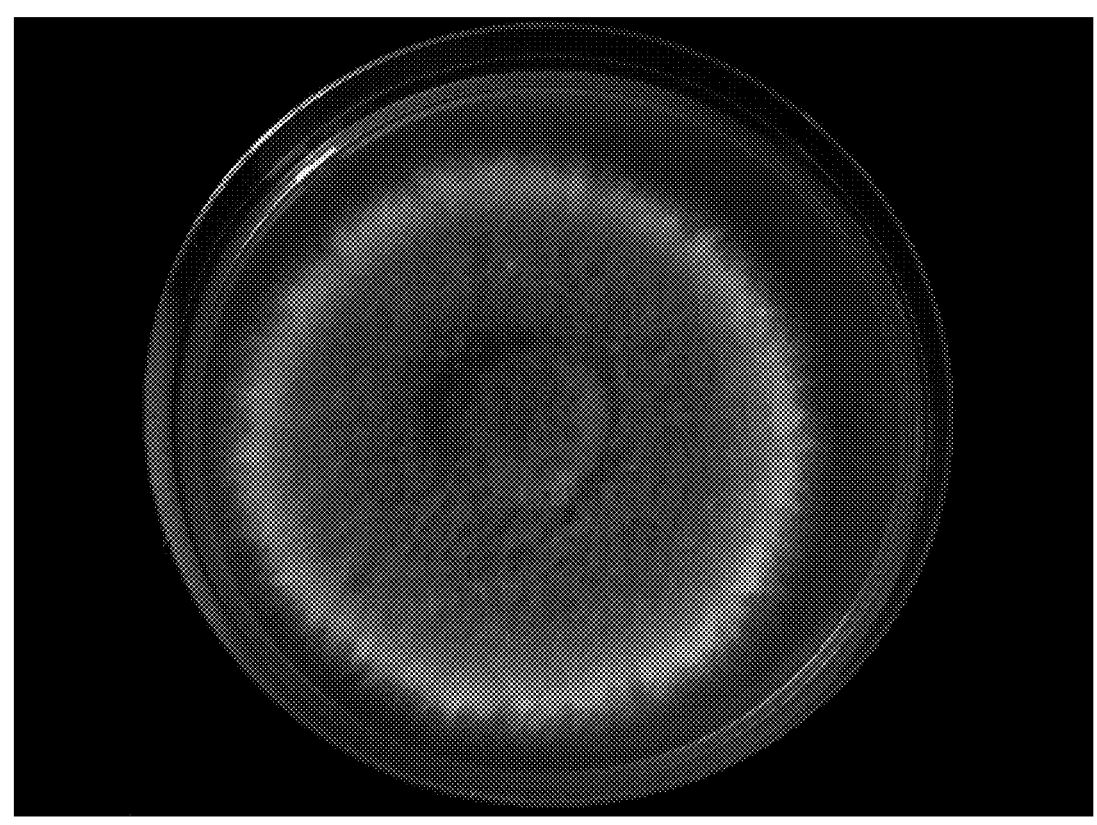
FIG. 1 illustrates a colony morphology of the *Bipolaris yamadae* (Y. Nisik.) Shoemaker strain HXDC-1-2.
Figure 2:
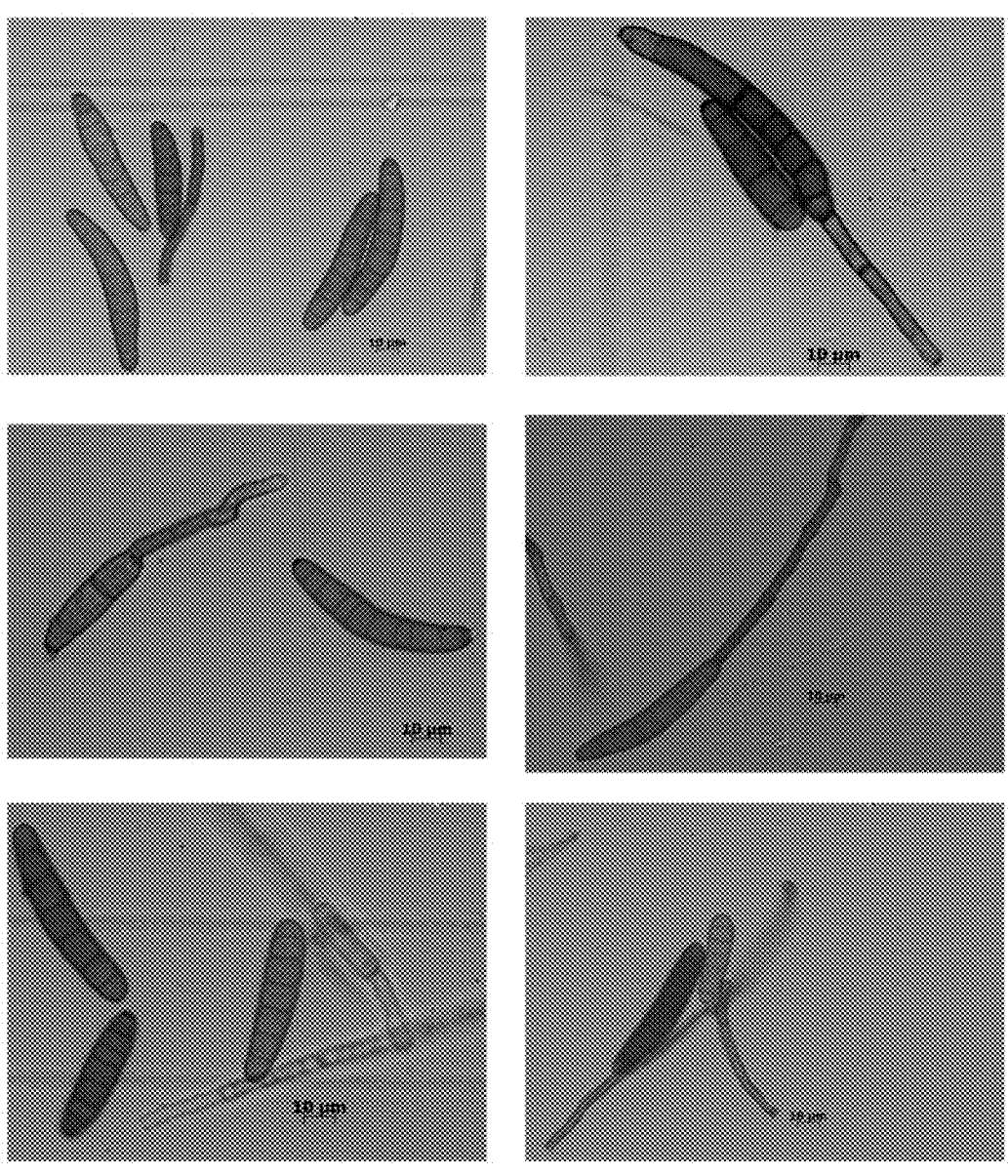
FIG. 2 illustrates a conidia morphology of the *Bipolaris yamadae* (Y. Nisik.) Shoemaker strain HXDC-1-2.

Provided is a *Bipolaris yamadae* (Y. Nisik.) Shoemaker strain (HXDC-1-2) (Preservation Unit: China General Microbiological Culture Collection Center; Address: No. 3, No. 1 Courtyard, Beichen West Road, Chaoyang District, Beijing; Date of Deposit: 10 May 2019; Preservation No.: CGMCC No. 17778), *Bipolaris yamadae* (Y. Nisik) Shoemaker strain belongs to the Fungi, Ascomycota, Dothideomycetes, Pleosporomycetidae, Pleosporales Luttrell ex Barr, Plesporaceae Nitschke, *Cochliobolus* Drechsler [asexual stage: *Bipolaris* Shoemarke], *Bipolaris yamadae* (Y. Nisik) Shoemaker). This strain grows rapidly on potato glucose medium, is cultured for 5 days under dark conditions at 28° C., has a colony diameter of 50 to 60 mm, is gray-black, is black-brown on the rear surface of the colony, and the colony does not contain any water-soluble pigment. As shown in FIG. 1, the colony morphology of *Bipolaris yamadae* (Y. Nisik.) Shoemaker after 5 days of cultivation is illustrated. The conidiophores are olive green or yellow-brown, are solitary or clustered, the conidiophores are light-colored, the conidiophores are in a curved shape of knee bending with the width ranging from 4.5 to 9.5 μm. The conidia are colored from yellow-brown to dark-brown, are quasi-spindle-shaped or inverted-club-shaped, and are straight or slightly curved, the middle portions of the conidia are slightly wider, and two apices of the conidia are slightly narrower, the basal cells of the conidia are blunt round, the outer surfaces of the basal cells are smooth, the basal cells have 6 to 9 pseudoseptum (mostly 7 to 8), the outer surfaces have an area of 54.5 to 92.5 μm×12.5 to 17.5 μm (on average of 69.5×14.7 μm). FIG. 2 illustrates the conidial morphology of *Bipolaris yamadae* (Y. Nisik.) Shoemaker under a high power microscope.

Embodiment 1

The new strain of the present disclosure was obtained through the following ways, the inventor investigated the incidence of *Microstegium vimineum* on the forest edge, grassland, wilderness, wetland, crop field edge, ditches, hedges, canyons and farmland in Anhui, Fujian, Guangdong, Guangxi, Guizhou, Henan, Hubei, Hunan, Jiangsu, Jiangxi, Sichuan, Shandong, Taiwan, Yunnan, Tibet and Zhejiang provinces in China, collected the diseased leaves of *Microstegium vimineum*, recorded the disease symptoms and relevant information of the plant and brought the information back to the laboratory, and then the inventor isolated and studied the parasitic fungi, and verified the pathogenicity in strict accordance with Koch's Postulate.

First of all, the pathogenic symptoms of the spores produced by the natural conditions of *Bipolaris yamadae* (Y. Nisik.) Shoemaker HXDC-1-2 on *Microstegium vimineum* are as follows: All of the diseased plant leaves of *Microstegium vimineum* have different sizes of disease spots. At the early stage of the disease, dark-brown or black disease spots in a round (0.25 cm to 0.40 cm in diameter) or oval (0.25 cm to 0.3 cm in width×0.4 cm to 0.5 cm in length) shape appear on the surface of the plant leaves, there are yellow or green halos on the edge of the plant leaves, and the tip and edge of the leaves are partially yellowed. At the middle stage of the disease, the disease spots gradually expand, the edges of the diseased leaves turn yellow to brown and are slightly curled, and the centers of some leaves turn yellow to brown. Finally, the disease spots become larger into a large brown or black area, and the leaves become yellow or curled until the whole plant dies.

The tissue pieces are cut from the diseased and healthy junctions of the diseased leaves and are disinfected with 75% alcohol and 1% sodium hypochlorite solution. These small pieces of tissue are inoculated on PDA medium, cultivated under dark conditions at 28° C. for 2 days, and the isolated strains are purified and cultivated. The observed mycelial growth situation and the observed conidia production situation are similar to those above, and the strains are the strong pathogenic fungus of *Microstegium vimineum*, the strains are stored on the slant medium at 4° C. for standby.

The morphology of conidia and conidiophores are observed under the optical microscope, and the sizes of conidia is determined by micrography. Pathogen identification is carried out according to the morphological characteristics described in "Chinese Fungi" and "Fungal Identification Manual". After identification, the morphological characteristics of strain HXDC-1-2 are basically consistent with the description of *Bipolaris yamadae* (Y. Nisik.) Shoemaker in Volume 30 of "Chinese Fungi", which is identified as *Bipolaris yamadae*. The description is as follows: the conidiophores are yellow-brown, are solitary or clustered, are branched sometimes, the apex of the conidiophores is light-colored, are in a curved shape of knee bending with the width of 4.5 μm to 9.5 Conidia are in a color from yellow-brown to dark-brown, are quasi-spindle-shaped or sometimes inverted-club-shaped, are straight or slightly curved, the middle portions of the conidia are slightly wider, and two apices of each of the conidia are slightly narrower, the basal cells of the conidia are blunt round, the outer surfaces of the basal cells are smooth, the basal cells have 6 to 9 pseudoseptum (mostly 7 to 8), the outer surfaces have an area of 54.5 μm to 92.5 μm×12.5 μm to 17.5 μm (on average of 69.5 μm×14.7 μm); The umbilicus is obvious and slightly prominent.

The fungal gDNA extraction kit (BIOMIGA) is used to extract pathogenic fungal DNA, and rDNA ITS sequence, GPDH sequence and EF1α sequence are used to perform PCR amplification respectively (Polymerase Chain Reaction). The general primers are as follows:

```
                                      (SEQ ID NO: 4)
ITS4 (5'-TCCTCCCGCTTATTGATGC-3'), (SEQ ID NO: 5)
ITS5 (5'-GGAAGTTAAAAGTCGTAAAGG-3'), (SEQ ID NO: 6)
GPD1 (5'-CAACGGCTTCGGTCGCATTG-3'), (SEQ ID NO: 7)
GPD2 (5'-GCCAAGCAGTTGGTTGTTGC-3'), (SEQ ID NO: 8)
EF1-983F (5'-GCYCYGGHCAYCGTGAYTTYAT-3'), (SEQ ID NO: 9)
EF1-2218R (5'-ATGACACRACRACRACRGCRACRGTTG-3').
```

Figure 3:
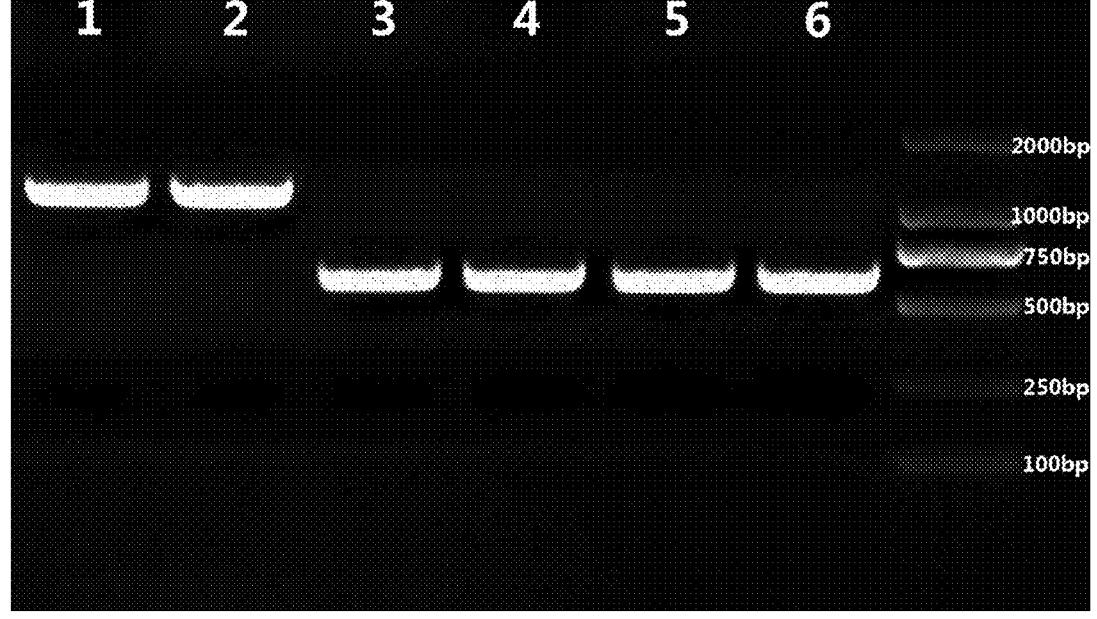
FIG. 3 illustrates a gel electrophoresis image of the *Bipolaris yamadae* (Y. Nisik.) Shoemaker strain HXDC-1-2, where 1 and 2 are EF1α sequences, 3 and 4 are ITS sequences, and 5 and 6 are GPDH sequences.

PCR products were extracted and purified with the DNA Gel/PCR Purification Miniprep Kit. The purified products were ligated to the pMD19 T-vector and transformed into *Escherichia coli* DH5a competent cells, white colonies are selected after blue and white spot screening and then are shaked. PCR amplification is carried out and is detected by the electrophoresis and gel analyzer. A single bright band is displayed on 2% agarose gel, as illustrated in FIGS. 3, 1 and 2 are EF1α amplified sequences, the size of the target band is about 800 bp; 3 and 4 are ITS amplified sequences, and the size of the target band is about 500 bp; 5 and 6 are GPDH amplified sequences, and the size of the target band is about 500 bp. The fungal fluid is entrusted to Sangon Biotech (Shanghai) Co., Ltd. for sequencing. The detected results are compared with the EF1a, ITS and GPDH related sequences of the nucleic acid database in Genbank (Blast software analysis). After amplification, sequencing and comparison, the homology of the EF1α amplified sequence with respect to *Bipolaris-yamadae*-model strain (ACCC36334) is 99%; the homology of the ITS amplified sequence with respect to *Bipolaris-yamadae*-model strain (CPC28807) is 99%; or when the homology of the GPDH amplified sequence and the *Bipolaris-yamadae*-model strain (CPC28807) is equal to or greater than 99%, it is determined that the strain is the *Bipolaris yamadae* Shoemaker strain. ITS amplified sequence is as shown in SEQ ID NO: 1, GPDH amplified sequence is as shown in SEQ ID NO: 2, and the EF1α amplified sequence is as shown in SEQ ID NO: 3.

The pathogenic symptoms of the spores produced by pure cultivation of *Bipolaris yamadae* (Y. Nisik.) Shoemaker HXDC-1-2 on *Microstegium vimineum* are as follows: the obvious dark-brown or black disease spots in a round or oval shape appear on the surface of the leaves, and some leaf tips or leaf margins appear yellowing. As time goes on, the disease spots gradually expand and the color becomes darker. In severe cases, the disease spots of the leaves are concentrated into patches, and the tops of the leaves die. At the later stage of inoculation, most of the leaves turn yellow or die, and the leaves become curled. The pathogen is re-isolated from the diseased leaves, and the spores on the surface of the diseased spots are consistent with the sprayed spores of *Bipolaris yamadae* (Y. Nisik.) Shoemaker spores, which is in accordance with Koch's Postulate.

The symptoms under the above experimental conditions are similar to those of natural diseases.

Although the *Bipolaris yamadae* (Y. Nisik.) Shoemaker HXDC-1-2 of the present disclosure is isolated from the *Microstegium vimineum*, it has a broad spectrum of gramineous weed pathogenicity. Another advantage is that it can effectively kill many annual and perennial Gramineous weeds without affecting the surrounding crops. From this point of view, although *Bipolaris yamadae* (Y. Nisik.) Shoemaker HXDC-1-2 has the same specificity as the chemical herbicide aromatic phenoxypropionic acid herbicide, it is safe for the environment.

According to their characteristics, they are identified as: Ascomycota, Dothiomycotes, Pleosporomycotidae, Pleosporales Luttrell ex Barr, Pleosporaceae Nitschke, *Cochliobolus* Drechsler [asexual stage: *Bipolaris* Shoemarke], and *Bipolaris yamadae* (Y. Nisik.) Shoemaker). This specialized strain mainly infects *Microstegium vimineum* and its relatives, as well as Gramineous weeds, and is highly immune to *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials, fruit trees and other crop fields. Among the 30 families 103 species crops or economic plants for the test, there are 33 species that are sensitive to *Bipolaris yamadae* (Y. Nisik.) shoemaker, 15 species that are slightly sensitive to the *Bipolaris yamadae* (Y. Nisik.) shoemaker, and 5 species that are insensitive to the *Bipolaris yamadae* (Y. Nisik.) shoemaker, of which most of the sensitive plants are concentrated in the *gramineae*, and other families of plants such as *leguminosae, cruciferae, pedaliaceae*, and some *gramineae* are weaker in the sensitivity to the *Bipolaris yamadae* (Y. Nisik.) Shoemaker. Therefore, the strain can be used in *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetable, flower, traditional Chinese medicinal materials, fruit tree and other crop fields, is used to control farmland weeds, including the grass weeds such as *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, and *Microstegium vimineum*; the annual *Sedge* such as *Cyperus iria* L., *Cyperus michelianus* (L.) Link, and *Cyperus compressus* L; the broad-leaved weeds such as *Humulus scandens* (Lour.) Merr., *Aeschynomene indica* L., *Chenopodium album* L. and *Chenopodium serotinum* L.

Embodiment 2

The *Bipolaris yamadae* (Y. Nisik.) Shoemaker strain HXDC-1-2 of the present disclosure is used for biological weed control. The specific application method is as follows: the strain is inoculated on the following media, sprayed on the field or weed occurrence site after being induced to produce the conidia with the dosage of $10^2$ to $10^6$ conidia/mL.

The cultivation method of *Bipolaris yamadae* (Y. Nisik.) Shoemaker HXDC-1-2 is cultivated in dark for about 4 days. When the cultivation dish is exposed to black light or incandescent light (24 h) under the aseptic condition, the medium will produce spores in the process of irradiation.

PDA medium-potato glucose agar medium

Potatoes 200 g

Glucose 20 g

Agar 20 g

Water 1 L

At present, there is no disclosure on the fungal herbicides of *Microstegium vimineum* in China and abroad. The research in this field provides a new and excellent way to solve the problem of controlling the weeds of *Microstegium vimineum* and *gramineae* weeds. The herbicide composition of the present disclosure can be used together with other suitable chemical herbicides, thereby reducing the amount of chemical herbicides and reducing the pollution on environment.

As required, the auxiliaries such as surfactants, stabilizers can be used in the herbicide composition of the present disclosure, surfactants such as Tween 20, Tween 80 can be used, and antioxidants and the like can be used as stabilizers.

Embodiment 3

The leaves of the diseased *Microstegium vimineum* are collected from the field, and the symptoms of the disease are recorded and examined under the microscope. The isolation of pathogenic fungi is carried out on the agar medium soaked in the solution of *Microstegium vimineum*. The single conidia of the strain are selected under the microscope, are inoculated on PDA medium, respectively, and are cultivated at 28° C. under dark conditions. The characteristics of pure cultured colonies of pathogenic fungi are observed and the diameters of colonies are measured. The colony discs with a diameter of 5 mm are inoculated in the center of the PDA plate, and the colony diameters are measured 4 days later.

TABLE 1

| Comparison of colony characteristics of pathogenic fungi of *Microstegium vimineum* | | | | | | | |
|---|---|---|---|---|---|---|---|
| | Identification | Collection | D1 | | | colony | |
| Strain | Results | location | (mm) | D2(mm) | Thickness | Color | Surface |
| Strain BJQZ-1-1 | *Bipolaris* | Bijie, Guizhou | 81.17 | 86.54 | ++ | steel gray | velvet |
| Strain NTHM-2-2 | *Bipolaris setariae* | Nantong, Jiangsu | 76.34 | 81.33 | + | crineous | velvet |
| Strain HXDC-1-2 | *Bipolaris yamadae* | Guiyang, Guizhou | 82.45 | 89.87 | ++ | dark gray | velvet |

Note:
D1 represents the colony diameter formed after 5 days of single conidium, and D2 represents the colony diameter formed after 4 days of 5 mm colony discs.

Embodiment 4

Pathogenic fungi are isolated from the diseased plants of *Microstegium vimineum* naturally occurring in Guiyang, Guizhou, and their pathogenicity is tested. Different concentrations of conidial suspension of various pathogenic fungi (among which the surfactant is Tween 20 and Tween 80, and the stabilizer is antioxidant) are sprayed on *Microstegium vimineum* under natural conditions to observe the pathogenic characteristics of fungi.

TABLE 2

| Comparison of pathogenicity of several pathogenic fungi isolated from *Microstegium vimineum* plants to *Microstegium vimineum* | | | | | |
|---|---|---|---|---|---|
| | Disease Severity | | | | |
| Strain | $10^5$ sp/mL | $10^4$ sp/mL | $10^3$ sp/mL | $10^2$ sp/mL | $10^1$ sp/mL |
| *Bipolaris* BJQZ-1-1 | $0.71 \pm 0.02Cc$ | $0.44 \pm 0.02Cc$ | $0.21 \pm 0.05Cc$ | $0.13 \pm 0.04Cc$ | $0.05 \pm 0.01Cc$ |
| *Bipolaris setariae* NTHM-2-2 | $0.78 \pm 0.03Bb$ | $0.55 \pm 0.02Bb$ | $0.37 \pm 0.02Bb$ | $0.23 \pm 0.02Bb$ | $0.11 \pm 0.02Bb$ |
| *Bipolaris yamadae* HXDC-1-2 | $0.95 \pm 0.01Aa$ | $0.87 \pm 0.03Aa$ | $0.65 \pm 0.08Aa$ | $0.31 \pm 0.03Aa$ | $0.19 \pm 0.02Aa$ |

Note:
$10^5$ and $10^4$ respectively indicate that the concentration of the sprayed conidial suspension is $10^5$ and $10^4$ conidia per milliliter (the same below).
The lowercase letter is 0.05 significant level, and the uppercase letter is 0.01 significant level (the same below).

It can be seen from Table 2 that the pathogenicity of *Bipolaris yamadae* HXDC-1-2 strains is higher than that of other strains.

Embodiment 5

HXDC-1-2 strain is cultured on PDA culture medium for 4 days, is exposed to the black light at 28° C. for irradiation, and the conidial suspension is prepared with sterile water (the same as Example 4). In addition, the seedlings of *Microstegium vimineum* are cultured in a pot with a diameter of 9 cm. When the seedlings reached the stage of 3 to 4 leaves, the conidial suspension is sprayed with a hand-held sprayer, and moisturized at 28° C. for 48 h and is kept the humidity at 80%. After one week of treatment, the weeds can be completely killed.

Embodiment 6

The seeds of the tested plants (see Table 3 and Table 4) are sowed in a pot with a diameter of 9 cm. Four groups of plants are repeatedly cultivated in the greenhouse at 28° C. When the tested plants reach the stage of 3 to 4 leaves, they shall be inoculated (the same as Examples 4 and 5), and 5 to 10 plants shall be reserved in each pot. The sensitivity of HXDC-1-2 strain to the tested plants are tested. The safety test results show that HXDC-1-2 strain is pathogenic to *Sorghum bicolor* (L.) Moench and *Vigna unguiculata* (L.) Walp., but not to *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials, fruit trees and other crops. The results of grass killing spectrum test show that HXDC-1-2 strain has strong pathogenicity to grass weeds such as *gramineae* weeds *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, *Microstegium vimineum, Microstegium* nodosum (Kom.) Tzvel. *Microstegium japonicum* (Miq.) Koidz., *Microstegium ciliatum* (Trin.) A. Camus.; *cyperaceae* weeds such as *Cyperus iria* L., *Cyperus michelianus* (L.) Link, *Cyperus compressus* L.; and broad-leaved weeds such as *Humulus scandens* (Lour.) Merr., *Aeschynomene indica* L., *Chenopodium album* L. and *Chenopodium serotinum* L. In addition, HXDC-1-2 strain has medium level pathogenicity to *Digitaria sanguinalis* (L.) Scop., *Eleusine indica* (L.) Gaertn., *Cyperus difformis* L., and the like. Therefore, HXDC-1-2 strain can be applied to *Oryza sativa* L., *Zea mays* L., *Glycine max* (L.) Merr., *Arachis hypogaea* L., *Sesamum*

*indicum* L., *Setaria italica* (L.) Beauv. var. *germanica* (Mill.) Schrad., *Vicia faba* L., *Pisum sativum* L., *Brassica napus* L. vegetables, flowers, traditional Chinese medicinal materials, fruit trees and other crop fields to prevent and control the grass weeds such as *Echinochloa crusgalli* (L.) Beauv., *Setaria viridis* (L.) Beauv., *Digitaria sanguinalis*, (L.) Scop., *Eleusine indica* (L.) Gaertn., *Leptochloa chinensis* (L.) Nees, *Leptochloa panicea* (Retz.) Ohwi, *Avena*

*fatua* L., *Alopecurus aequalis* Sobol., *Pseudosorghum zollingeri* (Steud.) A. Camus, *Microstegium vimineum*; the annual *Sedge* such as *Cyperus iria* L., *Cyperus michelianus* (L.) Link, *Cyperus compressus* L.; and the broad-leaved weeds such as *Humulus scandens* (Lour.) Merr., *Aeschynomene indica* L., *Chenopodium album* L. and *Chenopodium serotinum* L.

TABLE 3

| Sensitivity of tested crops to *Bipolaris yamadae* (Y. Nisik.) Shoemaker strain HXDC-1-2 | | | | |
|---|---|---|---|---|
| Family | Species | $10^5$ sp/mL | $10^4$ sp/mL | $10^3$ sp/mL |
| Gramineae | *Oryza sativa* L. (indica) | 0.09 ± 0.01Aa | 0.00 ± 0.00Bb | 0.00 ± 0.00Bb |
| | *Oryza sativa* L. (japonica) | 0.00 ± 0.00Aa | 0.00 ± 0.00Aa | 0.00 ± 0.00Aa |
| | *Zea mays* L. (fresh food) | 0.00 ± 0.00Aa | 0.00 ± 0.00Aa | 0.00 ± 0.00Aa |
| | *Zea mays* L. (fodder) | 0.00 ± 0.00Aa | 0.00 ± 0.00Aa | 0.00 ± 0.00Aa |
| | *Triticum aestivum* L. | 0.39 ± 0.02Aa | 0.18 ± 0.02Bb | 0.00 ± 0.00Cc |
| | *Setaria italica* (L.) Beauv. var. *germanica* (Mill.) Schrad. | 0.00 ± 0.00Aa | 0.00 ± 0.00Aa | 0.00 ± 0.00Aa |
| | *Hordeum vulgare* L. | 0.33 ± 0.06Aa | 0.23 ± 0.02Bb | 0.00 ± 0.00Cc |
| | *Sorghum bicolor* (L.) Moench | 0.55 ± 0.01Aa | 0.43 ± 0.02Bb | 0.23 ± 0.01Cc |
| Leguminosae | *Vicia faba* L. | 0.00 ± 0.00Aa | 0.00 ± 0.00Aa | 0.00 ± 0.00Aa |
| | *Arachis hypogaea* L. | 0.00 ± 0.00Aa | 0.00 ± 0.00Aa | 0.00 ± 0.00Aa |
| | *Glycine max* (L.) Merr. | 0.00 ± 0.00Aa | 0.00 ± 0.00Aa | 0.00 ± 0.00Aa |
| | *Pisum sativum* L. | 0.00 ± 0.00Aa | 0.00 ± 0.00Aa | 0.00 ± 0.00Aa |
| | *Vigna unguiculata* (L.) Walp. | 0.84 ± 0.02Aa | 0.65 ± 0.03Bb | 0.39 ± 0.02Cc |
| Pedaliaceae | *Sesamum indicum* L. | 0.00 ± 0.00Aa | 0.00 ± 0.00Aa | 0.00 ± 0.00Aa |
| Cruciferae | *Brassica napus* L. | 0.00 ± 0.00Aa | 0.00 ± 0.00Aa | 0.00 ± 0.00Aa |
| | *Brassica chinese* L. | 0.00 ± 0.00Aa | 0.00 ± 0.00Aa | 0.00 ± 0.00Aa |
| | *Capsella bursa-pastoris* (L.) Medic. | 0.00 ± 0.00Aa | 0.00 ± 0.00Aa | 0.00 ± 0.00Aa |
| | *Raphanus sativus* L. | 0.00 ± 0.00Aa | 0.00 ± 0.00Aa | 0.00 ± 0.00Aa |
| | *Brassica pekinensis* (Lour.) Rupr. | 0.00 ± 0.00Aa | 0.00 ± 0.00Aa | 0.00 ± 0.00Aa |
| Malvaceae | *Gossypium* spp L. | 0.16 ± 0.02Aa | 0.00 ± 0.00Bb | 0.00 ± 0.00Bb |
| Labiatae | *Nepeta cataria* L. | 0.00 ± 0.00Aa | 0.00 ± 0.00Aa | 0.00 ± 0.00Aa |
| | *Perilla frutescens* (L.) Britt. | 0.00 ± 0.00Aa | 0.00 ± 0.00Aa | 0.00 ± 0.00Aa |
| Solanaceae | *Capsicum annuum* L. | 0.00 ± 0.00Aa | 0.00 ± 0.00Aa | 0.00 ± 0.00Aa |
| | *Nicotiana tabacum* L. | 0.00 ± 0.00Aa | 0.00 ± 0.00Aa | 0.00 ± 0.00Aa |
| | *Solanum melongena* L. | 0.00 ± 0.00Aa | 0.00 ± 0.00Aa | 0.00 ± 0.00Aa |
| Cucurbitaceae | *Luffa cylindrica* (L.) Roem. | 0.00 ± 0.00Aa | 0.00 ± 0.00Aa | 0.00 ± 0.00Aa |
| Compositae | *Sonchus oleraceus* L. | 0.00 ± 0.00Aa | 0.00 ± 0.00Aa | 0.00 ± 0.00Aa |
| Myricaceae | *Myrica rubra* (Lour.) S. et Zucc. | 0.00 ± 0.00Aa | 0.00 ± 0.00Aa | 0.00 ± 0.00Aa |
| Family | Species | $10^2$ sp/mL | $10^1$ sp/mL | CK |
| Gramineae | *Oryza sativa* L. (indica) | 0.00 ± 0.00Bb | 0.00 ± 0.00Bb | 0.00 ± 0.00Bb |
| | *Oryza sativa* L. (japonica) | 0.00 ± 0.00Aa | 0.00 ± 0.00Aa | 0.00 ± 0.00Aa |
| | *Zea mays* L. (fresh food) | 0.00 ± 0.00Aa | 0.00 ± 0.00Aa | 0.00 ± 0.00Aa |
| | *Zea mays* L. (fodder) | 0.00 ± 0.00Aa | 0.00 ± 0.00Aa | 0.00 ± 0.00Aa |
| | *Triticum aestivum* L. | 0.00 ± 0.00Cc | 0.00 ± 0.00Cc | 0.00 ± 0.00Cc |
| | *Setaria italica* (L.) Beauv. var. *germanica* (Mill.) Schrad. | 0.00 ± 0.00Aa | 0.00 ± 0.00Aa | 0.00 ± 0.00Aa |
| | *Hordeum vulgare* L. | 0.00 ± 0.00Cc | 0.00 ± 0.00Cc | 0.00 ± 0.00Cc |
| | *Sorghum bicolor* (L.) Moench | 0.07 ± 0.01Dd | 0.00 ± 0.00Ee | 0.00 ± 0.00Ee |
| Leguminosae | *Vicia faba* L. | 0.00 ± 0.00Aa | 0.00 ± 0.00Aa | 0.00 ± 0.00Aa |
| | *Arachis hypogaea* L. | 0.00 ± 0.00Aa | 0.00 ± 0.00Aa | 0.00 ± 0.00Aa |
| | *Glycine max* (L.) Merr. | 0.00 ± 0.00Aa | 0.00 ± 0.00Aa | 0.00 ± 0.00Aa |
| | *Pisum sativum* L. | 0.00 ± 0.00Aa | 0.00 ± 0.00Aa | 0.00 ± 0.00Aa |
| | *Vigna unguiculata* (L.) Walp. | 0.17 ± 0.02Dd | 0.08 ± 0.01Ee | 0.00 ± 0.00Ff |
| Pedaliaceae | *Sesamum indicum* L. | 0.00 ± 0.00Aa | 0.00 ± 0.00Aa | 0.00 ± 0.00Aa |
| Cruciferae | *Brassica napus* L. | 0.00 ± 0.00Aa | 0.00 ± 0.00Aa | 0.00 ± 0.00Aa |
| | *Brassica chinese* L. | 0.00 ± 0.00Aa | 0.00 ± 0.00Aa | 0.00 ± 0.00Aa |
| | *Capsella bursa-pastoris* (L.) Medic. | 0.00 ± 0.00Aa | 0.00 ± 0.00Aa | 0.00 ± 0.00Aa |
| | *Raphanus sativus* L. | 0.00 ± 0.00Aa | 0.00 ± 0.00Aa | 0.00 ± 0.00Aa |
| | *Brassica pekinensis* (Lour.) Rupr. | 0.00 ± 0.00Aa | 0.00 ± 0.00Aa | 0.00 ± 0.00Aa |
| Malvaceae | *Gossypium* spp L. | 0.00 ± 0.00Bb | 0.00 ± 0.00Bb | 0.00 ± 0.00Bb |
| Labiatae | *Nepeta cataria* L. | 0.00 ± 0.00Aa | 0.00 ± 0.00Aa | 0.00 ± 0.00Aa |
| | *Perilla frutescens* (L.) Britt. | 0.00 ± 0.00Aa | 0.00 ± 0.00Aa | 0.00 ± 0.00Aa |
| Solanaceae | *Capsicum annuum* L. | 0.00 ± 0.00Aa | 0.00 ± 0.00Aa | 0.00 ± 0.00Aa |
| | *Nicotiana tabacum* L. | 0.00 ± 0.00Aa | 0.00 ± 0.00Aa | 0.00 ± 0.00Aa |
| | *Solanum melongena* L. | 0.00 ± 0.00Aa | 0.00 ± 0.00Aa | 0.00 ± 0.00Aa |
| Cucurbitaceae | *Luffa cylindrica* (L.) Roem. | 0.00 ± 0.00Aa | 0.00 ± 0.00Aa | 0.00 ± 0.00Aa |
| Compositae | *Sonchus oleraceus* L. | 0.00 ± 0.00Aa | 0.00 ± 0.00Aa | 0.00 ± 0.00Aa |
| Myricaceae | *Myrica rubra* (Lour.) S. et Zucc. | 0.00 ± 0.00Aa | 0.00 ± 0.00Aa | 0.00 ± 0.00Aa |

TABLE 4

Sensitivity of the tested weeds to *Bipolaris yamadae* (Y. Nisik.) Shoemaker strain HXDC-1-2

| Family | Species | $10^5$ sp/mL | $10^4$ sp/mL | $10^3$ sp/mL |
|---|---|---|---|---|
| Urticaceae | *Pouzolzia zeylanica* (L.) Benn. | 0.15 ± 0.04Aa | 0.09 ± 0.03ABa | 0.00 ± 0.00Bb |
| Vitaceae | *Cayratia japonica* (Thunb.) Gagnep. | 0.00 ± 0.00Aa | 0.00 ± 0.00Aa | 0.00 ± 0.00Aa |
| Gramineae | *Microstegium japonicum* (Miq.) Koidz. | 0.92 ± 0.02Aa | 0.81 ± 0.01Bb | 0.55 ± 0.03Cc |
| | *Pseudosorghum zollingeri* (Steud.) A. Camus | 0.85 ± 0.01Aa | 0.78 ± 0.01Bb | 0.50 ± 0.01Cc |
| | *Digitaria sanguinalis* (L.) Scop. | 0.76 ± 0.01Aa | 0.67 ± 0.01Bb | 0.41 ± 0.02Cc |
| | *Eleusine indica* (L.) Gaertn. | 0.68 ± 0.01Aa | 0.43 ± 0.01Bb | 0.25 ± 0.02Cc |
| | *Setaria viridis* (L.) Beauv. | 0.88 ± 0.01Aa | 0.67 ± 0.01Bb | 0.55 ± 0.01Cc |
| | *Echinochloa crusgalli* (L.) Beauv. | 0.91 ± 0.01Aa | 0.85 ± 0.01Bb | 0.54 ± 0.01Cc |
| | *Leptochloa chinensis* (L.) Nees | 0.90 ± 0.02Aa | 0.85 ± 0.01Bb | 0.59 ± 0.02Cc |
| | *Leptochloa panicea* (Retz.) Ohwi | 0.89 ± 0.01Aa | 0.82 ± 0.02Bb | 0.53 ± 0.03Cc |
| | *Microstegium nodosum* (Kom.) Tzvel. | 0.92 ± 0.02Aa | 0.83 ± 0.02Ab | 0.54 ± 0.02Bc |
| | *Arthraxon hispidus* (Thunb.) Makino. | 0.74 ± 0.02Aa | 0.54 ± 0.02Bb | 0.34 ± 0.02Cc |
| | *Poa annua* L. | 0.53 ± 0.05Aa | 0.30 ± 0.01Bb | 0.16 ± 0.01Cc |
| | *Alopecurus aequalis* Sobol. | 0.53 ± 0.02Aa | 0.44 ± 0.01Bb | 0.20 ± 0.02Cc |
| | *Microstegium ciliatum* (Trin.) A. Camus. | 0.90 ± 0.02Aa | 0.75 ± 0.02Bb | 0.59 ± 0.04Cc |
| | *Beckmannia syzigachne* (Steud.) Fern. | 0.00 ± 0.00Aa | 0.00 ± 0.00Aa | 0.00 ± 0.00Aa |
| | *Lolium perenne* L. | 0.88 ± 0.02Aa | 0.74 ± 0.03Bb | 0.51 ± 0.02Cc |
| | *Avena fatua* L. | 0.84 ± 0.02Aa | 0.74 ± 0.02Bb | 0.48 ± 0.02Cc |
| | *Pennisetum alopecuroides* (L.) Spreng. | 0.47 ± 0.03Aa | 0.33 ± 0.01Bb | 0.22 ± 0.01Cc |
| | *Phragmites australis* (Cav.) Trin. ex Steud. | 0.05 ± 0.01Aa | 0.00 ± 0.00Bb | 0.00 ± 0.00Bb |
| | *Cynodon dactylon* (L.) Pers. | 0.64 ± 0.02Aa | 0.46 ± 0.02Bb | 0.25 ± 0.03Cc |
| | *Sorghum sudanense* (Piper) Stapf | 0.86 ± 0.01Aa | 0.70 ± 0.01Bb | 0.47 ± 0.04Cc |
| Compositae | *Conyza sumatrensis* (Retz.) Walker | 0.00 ± 0.00Aa | 0.00 ± 0.00Aa | 0.00 ± 0.00Aa |
| | *Bidens tripartita* L. | 0.00 ± 0.00Aa | 0.00 ± 0.00Aa | 0.00 ± 0.00Aa |
| | *Erigeron annuus* (L.) Pers. | 0.65 ± 0.02Aa | 0.51 ± 0.01Bb | 0.27 ± 0.01Cc |
| | *Conyza canadensis* (L.) Cronq. | 0.23 ± 0.02Aa | 0.13 ± 0.01Bb | 0.04 ± 0.01Cc |
| | *Erigeron acer* L. | 0.00 ± 0.00Aa | 0.00 ± 0.00Aa | 0.00 ± 0.00Aa |
| | *Eclipta prostrata* (L.) L. | 0.00 ± 0.00Aa | 0.00 ± 0.00Aa | 0.00 ± 0.00Aa |
| | *Ambrosia artemisiifolia* L. | 0.00 ± 0.00Aa | 0.00 ± 0.00Aa | 0.00 ± 0.00Aa |
| | *Cirsium setosum* (Willd.) MB. | 0.45 ± 0.03Aa | 0.23 ± 0.03Bb | 0.14 ± 0.01Cc |
| | *Artemisia argyi* Levl. et Van. | 0.09 ± 0.02Aa | 0.00 ± 0.00Bb | 0.00 ± 0.00Bb |
| | *Artemisia selengensis* Turcz. ex Bess. | 0.73 ± 0.03Aa | 0.53 ± 0.01Bb | 0.31 ± 0.01Cc |
| | *Ageratine adenophora* (Spreng.) King and Rob. | 0.26 ± 0.02Aa | 0.13 ± 0.01Bb | 0.04 ± 0.01Cc |
| Verbenaceae | *Vitex negundo* L. | 0.00 ± 0.00Aa | 0.00 ± 0.00Aa | 0.00 ± 0.00Aa |
| Amaranthaceae | *Amaranthus spinosus* L. | 0.00 ± 0.00Aa | 0.00 ± 0.00Aa | 0.00 ± 0.00Aa |
| | *Amaranthus viridis* L. | 0.22 ± 0.02Aa | 0.13 ± 0.02Bb | 0.04 ± 0.02Cc |
| | *Amaranthus lividus* L. | 0.57 ± 0.05Aa | 0.37 ± 0.01Bb | 0.21 ± 0.01Cc |
| | *Alternanlhera philoxeroides* (Mart.) Griseb. | 0.31 ± 0.02Aa | 0.15 ± 0.02Bb | 0.08 ± 0.01Cc |
| | *Celosia argentea* L. | 0.32 ± 0.01Aa | 0.15 ± 0.01Bb | 0.06 ± 0.01Cc |
| Cyperaceae | *Cyperus microiria* Steud. | 0.82 ± 0.02Aa | 0.71 ± 0.01Bb | 0.46 ± 0.01Cc |
| | *Cyperus compressus* L. | 0.84 ± 0.02Aa | 0.75 ± 0.02Bb | 0.45 ± 0.02Cc |
| | *Cyperus iria* L. | 0.75 ± 0.01Aa | 0.67 ± 0.01Bb | 0.52 ± 0.01Cc |
| | *Juncellus serotinus* (Rottb.) C. B. Clarke | 0.00 ± 0.00Aa | 0.00 ± 0.00Aa | 0.00 ± 0.00Aa |
| | *Cyperus michelianus* (L.) Link | 0.77 ± 0.01Aa | 0.64 ± 0.02Bb | 0.39 ± 0.02Cc |
| | *Cyperus difformis* L. | 0.44 ± 0.02Aa | 0.25 ± 0.03Bb | 0.17 ± 0.01Cc |
| Euphorbiaceae | *Phyllanthus urinaria* L. | 0.34 ± 0.02Aa | 0.19 ± 0.01Bb | 0.07 ± 0.01Cc |
| | *Euphorbia maculata* L. | 0.00 ± 0.00Aa | 0.00 ± 0.00Aa | 0.00 ± 0.00Aa |
| | *Acalypha australis* L. | 0.00 ± 0.00Aa | 0.00 ± 0.00Aa | 0.00 ± 0.00Aa |
| | *Euphorbia helioscopia* L. | 0.00 ± 0.00Aa | 0.00 ± 0.00Aa | 0.00 ± 0.00Aa |
| Aizoaceae | *Mollugo stricta* L | 0.00 ± 0.00Aa | 0.00 ± 0.00Aa | 0.00 ± 0.00Aa |
| Commelinaceae | *Commelina communis* L. | 0.61 ± 0.04Aa | 0.32 ± 0.02Bb | 0.12 ± 0.01Cc |
| | *Commelina bengalensis* L. | 0.00 ± 0.00Aa | 0.00 ± 0.00Aa | 0.00 ± 0.00Aa |
| Sterculiaceae | *Melochia corchorifolia* L. | 0.33 ± 0.02Aa | 0.16 ± 0.01Bb | 0.03 ± 0.01Cc |
| Solanaceae | *Solanum nigrum* L. | 0.00 ± 0.00Aa | 0.00 ± 0.00Aa | 0.00 ± 0.00Aa |
| Ranunculaceae | *Ranunculus japonicus* Thunb. | 0.18 ± 0.01Aa | 0.10 ± 0.01Bb | 0.03 ± 0.01Cc |
| | *Ranunculus sieboldii* Miq. | 0.00 ± 0.00Aa | 0.00 ± 0.00Aa | 0.00 ± 0.00Aa |
| Scrophulariaceae | *Veronica persica* Poir. | 0.79 ± 0.01Aa | 0.64 ± 0.02Bb | 0.32 ± 0.01Cc |
| Moraceae | *Humulus scandens* (Lour.) Merr. | 0.89 ± 0.01Aa | 0.76 ± 0.02Bb | 0.52 ± 0.01Cc |
| Polygonaceae | *Polygonum hydropiper* L. | 0.00 ± 0.00Aa | 0.00 ± 0.00Aa | 0.00 ± 0.00Aa |
| | *Polygonum lapathifolium* L. | 0.00 ± 0.00Aa | 0.00 ± 0.00Aa | 0.00 ± 0.00Aa |
| Cruciferae | *Rorippa indica* (L.) Hiern. | 0.2 ± 0.01Aa | 0.10 ± 0.01Bb | 0.04 ± 0.01Cc |
| Umbelliferae | *Cnidium monnieri*(L.) Cuss. | 0.00 ± 0.00Aa | 0.00 ± 0.00Aa | 0.00 ± 0.00Aa |
| Leguminosae | *Aeschynomene indica* L. | 0.85 ± 0.02Aa | 0.75 ± 0.01Bb | 0.45 ± 0.02Cc |
| | *Medicago falcata* L. | 0.00 ± 0.00Aa | 0.00 ± 0.00Aa | 0.00 ± 0.00Aa |
| | *Medicago lupulina* L. | 0.00 ± 0.00Aa | 0.00 ± 0.00Aa | 0.00 ± 0.00Aa |
| | *Vicia gigantea* Bge. | 0.00 ± 0.00Aa | 0.00 ± 0.00Aa | 0.00 ± 0.00Aa |
| Labiatae | *Glechoma longituba* (Nakai) Kupr. | 0.00 ± 0.00Aa | 0.00 ± 0.00Aa | 0.00 ± 0.00Aa |
| Geraniaceae | *Geranium carolinianum* L. | 0.00 ± 0.00Aa | 0.00 ± 0.00Aa | 0.00 ± 0.00Aa |
| Pontederiaceae | *Monochoria vaginalis* (Burm.f.) Presl. | 0.18 ± 0.02Aa | 0.10 ± 0.02Bb | 0.04 ± 0.02Cc |
| Lythraceae | *Rotala indica* (Willd.) Koehne. | 0.00 ± 0.00Aa | 0.00 ± 0.00Aa | 0.00 ± 0.00Aa |
| | *Ammannia baccifera* L. | 0.00 ± 0.00Aa | 0.00 ± 0.00Aa | 0.00 ± 0.00Aa |
| Asclepiadaceae | *Metaplexis japonica* (Thunb.) Makino. | 0.74 ± 0.01Aa | 0.52 ± 0.01Bb | 0.25 ± 0.03Cc |
| Chenopodiaceae | *Chenopodium serotinum* L. | 0.94 ± 0.01Aa | 0.83 ± 0.01Bb | 0.52 ± 0.02Cc |
| | *Chenopodium album* L. | 0.90 ± 0.01Aa | 0.75 ± 0.01Bb | 0.47 ± 0.02Cc |
| Caryophyllaceae | *Myosoton aquaticum* (L.) Moench. | 0.00 ± 0.00Aa | 0.00 ± 0.00Aa | 0.00 ± 0.00Aa |

TABLE 4-continued

Sensitivity of the tested weeds to *Bipolaris yamadae* (Y. Nisik.) Shoemaker strain HXDC-1-2

| Family | Species | $10^2$ sp/mL | $10^1$ sp/mL | CK |
|---|---|---|---|---|
| Urticaceae | *Pouzolzia zeylanica* (L.) Benn. | 0.00 ± 0.00Bb | 0.00 ± 0.00Bb | 0.00 ± 0.00Bb |
| Vitaceae | *Cayratia japonica* (Thunb.) Gagnep. | 0.00 ± 0.00Aa | 0.00 ± 0.00Aa | 0.00 ± 0.00Aa |
| Gramineae | *Microstegium japonicum* (Miq.) Koidz. | 0.34 ± 0.02Dd | 0.10 ± 0.03Ee | 0.00 ± 0.00Ff |
| | *Pseudosorghum zollingeri* (Steud.) A. Camus | 0.24 ± 0.01Dd | 0.07 ± 0.01Ee | 0.00 ± 0.00Ff |
| | *Digitaria sanguinalis* (L.) Scop. | 0.16 ± 0.02Dd | 0.05 ± 0.01Ee | 0.00 ± 0.00Ef |
| | *Eleusine indica* (L.) Gaertn. | 0.12 ± 0.02Dd | 0.03 ± 0.01Ee | 0.00 ± 0.00Ef |
| | *Setaria viridis* (L.) Beauv. | 0.37 ± 0.02Dd | 0.16 ± 0.02Ee | 0.00 ± 0.00Ff |
| | *Echinochloa crusgalli* (L.) Beauv. | 0.36 ± 0.01Dd | 0.19 ± 0.01Ee | 0.00 ± 0.00Ff |
| | *Leptochloa chinensis* (L.) Nees | 0.29 ± 0.02Dd | 0.11 ± 0.01Ee | 0.00 ± 0.00Ff |
| | *Leptochloa panicea* (Retz.) Ohwi | 0.24 ± 0.02Dd | 0.09 ± 0.01Ee | 0.00 ± 0.00Ff |
| | *Microstegium nodosum* (Kom.) Tzvel. | 0.34 ± 0.01Cd | 0.13 ± 0.04De | 0.00 ± 0.00Ef |
| | *Arthraxon hispidus* (Thunb.) Makino. | 0.16 ± 0.02Dd | 0.06 ± 0.02Ee | 0.00 ± 0.00Ff |
| | *Poa annua* L. | 0.06 ± 0.01Dd | 0.01 ± 0.00Dd | 0.00 ± 0.00Dd |
| | *Alopecurus aequalis* Sobol. | 0.10 ± 0.01Dd | 0.00 ± 0.00Ee | 0.00 ± 0.00Ee |
| | *Microstegium ciliatum* (Trin.) A. Camus. | 0.30 ± 0.02Dd | 0.14 ± 0.02Ee | 0.00 ± 0.00Ff |
| | *Beckmannia syzigachne* (Steud.) Fern. | 0.00 ± 0.00Aa | 0.00 ± 0.00Aa | 0.00 ± 0.00Aa |
| | *Lolium perenne* L. | 0.30 ± 0.01Dd | 0.12 ± 0.02Ee | 0.00 ± 0.00Ff |
| | *Avena fatua* L. | 0.23 ± 0.01Dd | 0.08 ± 0.01Ee | 0.00 ± 0.00Ff |
| | *Pennisetum alopecuroides* (L.) Spreng. | 0.16 ± 0.01Dd | 0.07 ± 0.01Ee | 0.00 ± 0.00Ff |
| | *Phragmites australis* (Cav.) Trin. ex Steud. | 0.00 ± 0.00Bb | 0.00 ± 0.00Bb | 0.00 ± 0.00Bb |
| | *Cynodon dactylon* (L.) Pers. | 0.15 ± 0.03Cd | 0.04 ± 0.02De | 0.00 ± 0.00De |
| | *Sorghum sudanense* (Piper) Stapf | 0.35 ± 0.01Dd | 0.12 ± 0.01Ee | 0.00 ± 0.00Ff |
| Compositae | *Conyza sumatrensis* (Retz.) Walker | 0.00 ± 0.00Aa | 0.00 ± 0.00Aa | 0.00 ± 0.00Aa |
| | *Bidens tripartita* L. | 0.00 ± 0.00Aa | 0.00 ± 0.00Aa | 0.00 ± 0.00Aa |
| | *Erigeron annuus* (L.) Pers. | 0.15 ± 0.01Dd | 0.00 ± 0.00Ee | 0.00 ± 0.00Ee |
| | *Conyza canadensis* (L.) Cronq. | 0.00 ± 0.00Cd | 0.00 ± 0.00Cd | 0.00 ± 0.00Cd |
| | *Erigeron acer* L. | 0.00 ± 0.00Aa | 0.00 ± 0.00Aa | 0.00 ± 0.00Aa |
| | *Eclipta prostrata* (L.) L. | 0.00 ± 0.00Aa | 0.00 ± 0.00Aa | 0.00 ± 0.00Aa |
| | *Ambrosia artemisiifolia* L. | 0.00 ± 0.00Aa | 0.00 ± 0.00Aa | 0.00 ± 0.00Aa |
| | *Cirsium setosum* (Willd.) MB. | 0.02 ± 0.02Dd | 0.00 ± 0.00Dd | 0.00 ± 0.00Dd |
| | *Artemisia argyi* Levl. et Van. | 0.00 ± 0.00Bb | 0.00 ± 0.00Bb | 0.00 ± 0.00Bb |
| | *Artemisia selengensis* Turcz. ex Bess. | 0.12 ± 0.01Dd | 0.03 ± 0.01Ee | 0.00 ± 0.00Ee |
| | *Ageratine adenophora* (Spreng.) King and Rob. | 0.00 ± 0.00Cd | 0.00 ± 0.00Cd | 0.00 ± 0.00Cd |
| Verbenaceae | *Vitex negundo* L. | 0.00 ± 0.00Aa | 0.00 ± 0.00Aa | 0.00 ± 0.00Aa |
| Amaranthaceae | *Amaranthus spinosus* L. | 0.00 ± 0.00Aa | 0.00 ± 0.00Aa | 0.00 ± 0.00Aa |
| | *Amaranthus viridis* L. | 0.00 ± 0.00Cc | 0.00 ± 0.00Cc | 0.00 ± 0.00Cc |
| | *Amaranthus lividus* L. | 0.07 ± 0.02Dd | 0.01 ± 0.01Dd | 0.01 ± 0.01Dd |
| | *Alternanlhera philoxeroides* (Mart.) Griseb. | 0.00 ± 0.00Dd | 0.00 ± 0.00Dd | 0.00 ± 0.00Dd |
| | *Celosia argentea* L. | 0.00 ± 0.00Dd | 0.00 ± 0.00Dd | 0.00 ± 0.00Dd |
| Cyperaceae | *Cyperus microiria* Steud. | 0.14 ± 0.01Dd | 0.04 ± 0.01Ee | 0.00 ± 0.00Ef |
| | *Cyperus compressus* L. | 0.2 ± 0.01Dd | 0.06 ± 0.01Ee | 0.00 ± 0.00Ef |
| | *Cyperus iria* L. | 0.21 ± 0.04Dd | 0.05 ± 0.01Ee | 0.00 ± 0.00Ef |
| | *Juncellus serotinus* (Rottb.) C. B. Clarke | 0.00 ± 0.00Aa | 0.00 ± 0.00Aa | 0.00 ± 0.00Aa |
| | *Cyperus michelianus* (L.) Link | 0.2 ± 0.02Dd | 0.05 ± 0.01Ee | 0.00 ± 0.00Ef |
| | *Cyperus difformis* L. | 0.05 ± 0.02Dd | 0.00 ± 0.00De | 0.00 ± 0.00De |
| Euphorbiaceae | *Phyllanthus urinaria* L. | 0.01 ± 0.00Dd | 0.00 ± 0.00Dd | 0.00 ± 0.00Dd |
| | *Euphorbia maculata* L. | 0.00 ± 0.00Aa | 0.00 ± 0.00Aa | 0.00 ± 0.00Aa |
| | *Acalypha australis* L. | 0.00 ± 0.00Aa | 0.00 ± 0.00Aa | 0.00 ± 0.00Aa |
| | *Euphorbia helioscopia* L. | 0.00 ± 0.00Aa | 0.00 ± 0.00Aa | 0.00 ± 0.00Aa |
| Aizoaceae | *Mollugo stricta* L | 0.00 ± 0.00Aa | 0.00 ± 0.00Aa | 0.00 ± 0.00Aa |
| Commelinaceae | *Commelina communis* L. | 0.00 ± 0.00Dd | 0.00 ± 0.00Dd | 0.00 ± 0.00Dd |
| | *Commelina bengalensis* L. | 0.00 ± 0.00Aa | 0.00 ± 0.00Aa | 0.00 ± 0.00Aa |
| Sterculiaceae | *Melochia corchorifolia* L. | 0.00 ± 0.00Cd | 0.00 ± 0.00Cd | 0.00 ± 0.00Cd |
| Solanaceae | *Solanum nigrum* L. | 0.00 ± 0.00Aa | 0.00 ± 0.00Aa | 0.00 ± 0.00Aa |
| Ranunculaceae | *Ranunculus japonicus* Thunb. | 0.00 ± 0.00Cd | 0.00 ± 0.00Cd | 0.00 ± 0.00Cd |
| | *Ranunculus sieboldii* Miq. | 0.00 ± 0.00Aa | 0.00 ± 0.00Aa | 0.00 ± 0.00Aa |
| Scrophulariaceae | *Veronica persica* Poir. | 0.08 ± 0.02Dd | 0.00 ± 0.00Ee | 0.00 ± 0.00Ee |
| Moraceae | *Humulus scandens* (Lour.) Merr. | 0.28 ± 0.02Dd | 0.12 ± 0.02Ee | 0.00 ± 0.00Ff |
| Polygonaceae | *Polygonum hydropiper* L. | 0.00 ± 0.00Aa | 0.00 ± 0.00Aa | 0.00 ± 0.00Aa |
| | *Polygonum lapathifolium* L. | 0.00 ± 0.00Aa | 0.00 ± 0.00Aa | 0.00 ± 0.00Aa |
| Cruciferae | *Rorippa indica* (L.) Hiern. | 0.00 ± 0.00Dd | 0.00 ± 0.00Dd | 0.00 ± 0.00Dd |
| Umbelliferae | *Cnidium monnieri*(L.) Cuss. | 0.00 ± 0.00Aa | 0.00 ± 0.00Aa | 0.00 ± 0.00Aa |
| Leguminosae | *Aeschynomene indica* L. | 0.18 ± 0.01Dd | 0.09 ± 0.01Ee | 0.00 ± 0.00Ff |
| | *Medicago falcata* L. | 0.00 ± 0.00Aa | 0.00 ± 0.00Aa | 0.00 ± 0.00Aa |
| | *Medicago lupulina* L. | 0.00 ± 0.00Aa | 0.00 ± 0.00Aa | 0.00 ± 0.00Aa |
| | *Vicia gigantea* Bge. | 0.00 ± 0.00Aa | 0.00 ± 0.00Aa | 0.00 ± 0.00Aa |
| Labiatae | *Glechoma longituba* (Nakai) Kupr. | 0.00 ± 0.00Aa | 0.00 ± 0.00Aa | 0.00 ± 0.00Aa |
| Geraniaceae | *Geranium carolinianum* L. | 0.00 ± 0.00Aa | 0.00 ± 0.00Aa | 0.00 ± 0.00Aa |
| Pontederiaceae | *Monochoria vaginalis* (Burm.f.) Presl. | 0.00 ± 0.00Cd | 0.00 ± 0.00Cd | 0.00 ± 0.00Cd |
| Lythraceae | *Rotala indica* (Willd.) Koehne. | 0.00 ± 0.00Aa | 0.00 ± 0.00Aa | 0.00 ± 0.00Aa |
| | *Ammannia baccifera* L. | 0.00 ± 0.00Aa | 0.00 ± 0.00Aa | 0.00 ± 0.00Aa |
| Asclepiadaceae | *Metaplexis japonica* (Thunb.) Makino. | 0.13 ± 0.01Dd | 0.03 ± 0.01Ee | 0.00 ± 0.00Ee |
| Chenopodiaceae | *Chenopodium serotinum* L. | 0.22 ± 0.01Dd | 0.07 ± 0.02Ee | 0.00 ± 0.00Ff |
| | *Chenopodium album* L. | 0.24 ± 0.02Dd | 0.04 ± 0.01Ee | 0.00 ± 0.00Ee |
| Caryophyllaceae | *Myosoton aquaticum* (L.) Moench. | 0.00 ± 0.00Aa | 0.00 ± 0.00Aa | 0.00 ± 0.00Aa |

What is claimed is:

1. A method of adopting a *Bipolaris yamadae* strain as a biological herbicide, comprising inoculating conidia of the *Bipolaris yamadae* strain with a conidium concentration of equal to or greater than $10^2$ conidia/ml on target weeds of a crop field, wherein the *Bipolaris yamadae* strain is a *Bipolaris yamadae* strain HXDC-1-2 and is preserved in China General Microbiological Culture Collection Center with a preservation number CGMCC No. 17778.

2. The method according to claim 1, wherein the target weeds include at least one of Gramineae weeds, *Sedge* weeds and broad-leaf weeds, wherein the Gramineae weeds include at least one of the *Echinochloa crusgalli* (L.) Beauv., *Setaria viridis* (L.) Beauv., *Digitaria sanguinalis* (L.) Scop., *Eleusine indica* (L.) Gaertn., *Leptochloa chinensis* (L.) Nees, *Leptochloa panicea* (Retz.) Ohwi, *Avena fatua* L., *Alopecurus aequalis* Sobol., *Pseudosorghum zollingeri* (Steud.) A. Camus, *Microstegium vimineum* and relatives of the *Microstegium vimineum*; the *Sedge* weeds include at least one of *Cyperus* iria L., *Cyperus michelianus* (L.) Link, *Cyperus compressus* L.; the broad-leaf weeds include at least one of *Humulus scandens* (Lour.) Merr., *Aeschynomene indica* L., *Chenopodium album* L. and *Chenopodium serotinum* L.

3. The method according to claim 2, wherein the relatives of the *Microstegium vimineum* includes at least one of the *Microstegium nodosum* (Kom.) Tzvel., *Microstegium ciliatum* (Trin.) A. Camus, *Microsteglum japonicum*, and *Arthraxon hispidus* (Thunb.) Makino.

4. The method according to claim 1, wherein the crops in the crop field include at least one of *Oryza sativa* L., *Zea mays* L., *Glycine max* (L.) Merr., *Arachis hypogaea* L., *Sesamum indicum* L., *Setaria italica* (L.) Beauv. var. *germanica* (Mill.) Schrad., *Vicia faba* L., *Pisum sativum* L., *Brassica napus* L., vegetables, flowers, traditional Chinese medicinal materials and fruit trees.

5. The method according to claim 4, wherein the vegetables is at least one of *Brassica chinese* L., *Brassica pekinensis* (Lour.) Rupr., *Raphanus sativus* L., Luffa *cylindrica* (L.) Roem., *Solanum melongena* L., *Capsicum annuum* L.; the traditional Chinese medicinal material-includes is at least one of *Perilla frutescens* (L.) Britt., *Nepeta cataria* L. and *Glechoma longituba* (Nakai) Kupr.; the fruit trees is *Myrica rubra* (Lour.) S. et Zucc.

\* \* \* \* \*